US008821542B2

(12) United States Patent
Zirps et al.

(10) Patent No.: US 8,821,542 B2
(45) Date of Patent: Sep. 2, 2014

(54) SUTURE MANAGEMENT SYSTEM (75) Inventors: Christopher T Zirps, Sharon, MA (US); Charles S Brunner, North Reading, MA (US); Jeffrey S Hovis, Boston, MA (US); Chris Kilburn-Peterson, Needham, MA (US)

(73) Assignee: DePuy Mitek, LLC, Raynham, MA (US)

( * ) Notice: Subject to any disclaimer, the term of this patent is extended or adjusted under 35 U.S.C. 154(b) by 1698 days.

(21) Appl. No.: 11/857,486

(22) Filed: Sep. 19, 2007

(65) Prior Publication Data
US 2008/0103528 A1    May 1, 2008

Related U.S. Application Data (60) Provisional application No. 60/855,628, filed on Oct. 31, 2006.

(51) Int. Cl.
*A61B 17/04*    (2006.01)

(52) U.S. Cl.
USPC .......................................................... 606/232

(58) Field of Classification Search
USPC .................................. 606/232, 151, 300–321
See application file for complete search history.

(56) References Cited

U.S. PATENT DOCUMENTS

| 3,949,755 | A  | * | 4/1976  | Vauquois ...................... 606/229 |
| 6,156,039 | A  |   | 12/2000 | Thal |
| 6,517,578 | B2 | * | 2/2003  | Hein ........................... 623/13.13 |
| 2002/0169478 | A1 | * | 11/2002 | Schwartz et al. ............. 606/232 |
| 2003/0130694 | A1 | * | 7/2003  | Bojarski et al. ............... 606/228 |
| 2005/0033366 | A1 | * | 2/2005  | Cole et al. ..................... 606/232 |
| 2006/0122608 | A1 | * | 6/2006  | Fallin et al. .................... 606/72 |
| 2010/0036395 | A1 | * | 2/2010  | Miller ........................... 606/139 |

FOREIGN PATENT DOCUMENTS

| EP | 1611852 | 1/2006 |
| WO | WO-9737595 | 10/1997 |
| WO | WO-0139671 | 6/2001 |
| WO | WO 02/36020 | 5/2002 |
| WO | WO-2004037094 | 5/2004 |
| WO | WO-2006037131 | 4/2006 |

\* cited by examiner

*Primary Examiner* — Corrine M McDermott
*Assistant Examiner* — Christopher L Templeton (57) ABSTRACT

Assemblies, devices and methods are provided for suture management associated with surgical procedures for anchoring suture to bone. Suture elements mounted to suture anchors are terminated in suture loops or tags, and associated stop members that in combination with visual coding provide suture identification, prevent accidental unmounting of suture from suture anchors, and reduce the number of suture legs requiring active management during complex arthroscopic repairs. The present invention also provides exemplary drivers that can be used with the various methods and devices disclosed herein, or with other methods and devices known in the art.

9 Claims, 5 Drawing Sheets

FIG. 5a _PRIOR ART_

SUTURE MANAGEMENT SYSTEM

REFERENCE TO RELATED APPLICATION

This application claims priority from U.S. Provisional Patent Application Ser. No. 60/855,628, filed on Oct. 31, 2006, entitled "Suture Management System", which is expressly incorporated by reference herein.

FIELD OF THE INVENTION

The present invention relates generally to medical devices and procedures, and more particularly to systems and methods for attaching soft tissue to bone.

BACKGROUND OF THE INVENTION

The complete or partial detachment of ligaments, tendons or other soft tissues from their associated bones within the body are relatively commonplace injuries. Such injuries are generally the result of excessive stresses being placed on these tissues. By way of example, tissue detachment may occur as the result of an accident such as a fall, overexertion during a work-related activity, during the course of an athletic event, repetitive stress, or in any one of many other situations and activities.

In the case of a partial detachment, the injury may heal itself, if given sufficient time and provided that care is taken not to expose the injury to further undue stress. In many cases, however, surgery may be needed to reattach the soft tissue to its associated bone or bones. Numerous devices are currently available to reattach the soft tissue to bone. Examples of currently available devices include screws, staples, tacks and suture anchors.

In soft tissue reattachment procedures utilizing suture anchors, one or more anchors, each bearing one or more strands of suture, are deployed in the bone in the desired area of tissue reattachment. The suture may be mounted to the suture anchor by passing through an eyelet associated with the suture anchor, about a portion of the suture anchor, or by in another conventional manner. Free ends or loops of the suture are passed through or around the soft tissue and are used to tie or otherwise secure the soft tissue to the bone. A surgical needle is typically mounted to one end of each suture strand to facilitate passage of the suture through tissue.

Complex or extensive surgical repairs may require the use of several suture anchors and up to several times as many free suture ends. In these procedures, tracking of individual suture strands and their relationship to one another, that is, suture management, can present particular challenges for a surgeon, particularly since such procedures are often arthroscopically performed using remote visualization. The surgeon must be able to identify which suture ends are associated with each suture anchor and with each other, to properly execute a repair and to ensure that a suture is not accidentally demounted from an anchor. In arthroscopic repair procedures, suture management can be particularly difficult because the visibility of the anchors at the surgical site, and of the sutures associated with the anchors, may be very limited. In addition, simply the presence of a large number of suture strands extending from a surgical site can result in physical and visual clutter, further increasing the difficulty of the surgical procedure for the surgeon, and presenting a risk of tangling sutures. Color-coding or otherwise visually marking sutures for identification is known in this art, but can provide only limited relief of these suture management issues, particularly when a required type of suture is available in only a very limited number of visually distinct colors or patterns, and several similarly loaded multi-suture anchors are deployed during a procedure. In addition, visual coding of sutures by itself does not reduce physical or visual clutter associated with a multiplicity of sutures deployed at the surgical site. Yet another factor is the speed and efficiency in which the procedure is performed. The patient is typically best served by being under anesthesia for the shortest possible period of time. Difficulties in managing sutures can complicate and prolong the duration of a procedure.

Accordingly, there remains a need for improved methods and devices for managing sutures in surgical procedures for repairing soft tissue to bone.

SUMMARY OF THE INVENTION

One aspect of the present invention is a surgical repair assembly. The assembly includes a suture anchor having a body, at least one suture engagement member such as an eyelet on or associated with at least a portion of the anchor body for passing suture, and at least one fixation element on the body for engaging bone A suture element can be passed through each eyelet. Each suture element has a first end, a second end and a suture diameter adapted for passing slidably through the respective eyelet. The first end terminates in a suture loop or a tag, and a stop member is positioned substantially adjacent to the loop or tag along the suture element, the stop member preventing the suture element from sliding entirely through the respective eyelet. In an embodiment, the first end and the second end of each suture element are visually coded for identification with one another.

In embodiments including two or more suture elements mounted on an anchor, the suture elements are visually coded to uniquely identify each element. The surgical repair assembly can also include a suture anchor installation tool having a proximal handle, a distal anchor engagement member for driving the suture anchor into bone, and a longitudinally slotted shaft therebetween, the slotted shaft being adapted for retaining at least one loop or tag and respective stop member.

Another aspect of the present invention is a method for reattaching soft tissue to a bone, The method includes providing a suture anchor having a suture mounted thereto via a suture engagement member, for example, through an eyelet. A suture element is positioned slidably through the member or eyelet. The suture element has a first end and a second end, the first end terminating in a suture loop secured by a knot formed in the suture element. The knot is sized to prevent its passage through the member or eyelet. The method further comprises fixing the suture anchor into the bone, sliding the suture element through the member eyelet to position the knot and the loop adjacent to the member or eyelet, and grasping and pulling the loop to position the suture element for securing the tissue to the bone. The method further includes using the suture element to secure the tissue to the bone. Securing the tissue to bone can be performed using surgical knots or other suture securing methods.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides suture anchor assemblies, methods and devices for anchoring suture to bone. The assemblies, methods and devices of the present invention provide for the management of suture routing, positioning and identification during surgical procedures, with particular application to procedures that include the approximation of soft tissue to bone using one or more suture anchors having one or more suture elements mounted thereto. The present invention also has particular application to arthroscopic surgery, although there is utility in other surgical procedures as well, such as open procedures.

As disclosed herein, various features can be formed on at least one end of a suture element that is used with a suture anchor assembly. Examples of such features, as described below, include tags and loops. Although embodiments of suture anchor assemblies with tags and loops are discussed separately, one skilled in the art will appreciate that a surgical procedure typically uses more than one suture anchor assembly, and that in any given surgical procedure, the suture elements can include the same types of features or different types of features.

Figure 1:
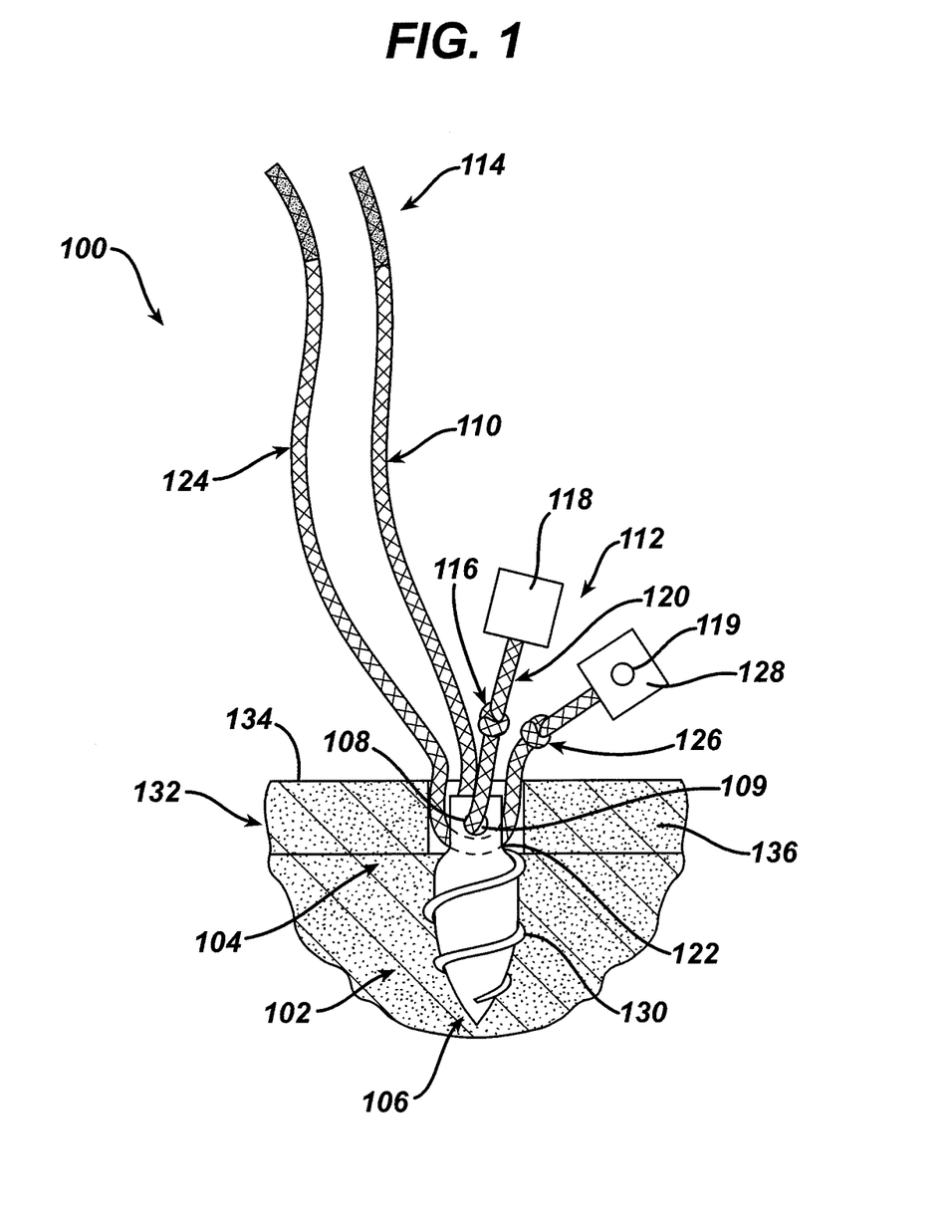
FIG. 1 illustrates an embodiment of a suture anchor assembly according to the present invention including sutures terminating in tags and mounted to a suture anchor.

A tag-terminated suture anchor assembly 100 according to one embodiment of the present invention is illustrated in FIG. 1. The assembly 100 includes a suture anchor 102 having a proximal end 104, a distal end 106 and first eyelet 108 having opening 109. A first surgical suture element or suture 110 having a first end 112 and a second end 114 can be slidably mounted through the opening 109 of first eyelet 108.

The first end 112 of the first suture element 110 can include a first stop member 116 and a first tag 118. In one embodiment, the first stop member 116 is dimensioned so that it cannot readily pass through the first eyelet 108, thereby preventing the first suture element 110 from being accidentally demounted from the anchor 102 by pulling the second end 114 of the first suture element 110. The first stop member 116 and the first tag 118 can be constructed from any materials compatible with positioning in a living body during a surgical procedure, i.e., biocompatible materials. The first stop member 116 is sized to prevent passage through the first eyelet 108. In one embodiment, the first stop member 116 is a knot in the first suture element 110. In other embodiments, the first stop member 116 is one of a crimp, a bead bonded to the first suture element, heat shrinkable tubing, a compression fitting, a molded section of the suture, or another type of equivalent stop member. The first stop member 116 can also be visually coded using color, shape, pattern or size to distinguish it from a stop member on another suture element, to associate it with another portion of the first suture element 110. For example, the second end 114 of the first suture element 110, or to associate it with the first tag 118. If desired, multiple stop members may be mounted on or formed into the end of the suture.

The first tag 118 provides a visual indicator of the position of the first end 112 of the first suture element 110, identification of the first tag 118 with the second end 114 of the first suture element 110, a visual code to distinguish the first suture element 110 from another suture element, and a surface for convenient grasping by the surgeon using forceps or another surgical tool, for manipulating the first suture element 110. Multiple tags may be mounted to the end of the suture if desired. Any kind of visual code compatible with use in a surgical field can be used, including a color code, a visual pattern displayed on the first tag 118, or incorporated into the shape of the first tag 118. Suture markings for visual coding can incorporate colored wax, markers, additional tags, or other means. In one embodiment, at least one of the first stop member 116 and the first tag 118 is visually coded for identification with the second end 114 of the first suture element. For example, a color coding, shape or other identifying characteristics of the tag can match a color coding, shape or other identifying characteristic on the second end of the suture element. The first tag 118 is sized for visibility and for convenience of grasping during the surgical procedure. In one embodiment, the first tag 118 has a maximum dimension of about 10 mm. In another embodiment, the first tag 118 can include an aperture for engagement by a hook, a surgical grasper, or for passing another suture element therethrough. In one embodiment, the first tag 118 is spaced apart from the first stop member 116 by a segment of suture 120 along the first suture element 110. In another embodiment, the first stop member 116 and the first tag 118 are positioned adjacent to one another along the first suture element 110. In yet another embodiment, the first stop member 116 is integral with the first flag 118. If desired, tactile elements may be formed into or mounted to the tag. In addition, at least one tag can optionally have one or more holes 119 formed therein. If present, such that a suture element is able to pass therethrough.

A suture anchor used in suture anchor assemblies of the present invention can include a plurality of eyelets or other structures for mounting suture. In addition, a single suture eyelet of an anchor can be sized to pass two or more sutures, while corresponding stop members are sized to prevent either of the two or more sutures from being demounted through the eyelet. In one embodiment, the suture anchor 102 can include a second eyelet 122 with a second suture element 124 mounted slidably therethrough. Further, the second suture element 124 can be structurally similar to the first suture element 110, but may differ in color or visible pattern from the first suture element 110. The second suture element 124 includes a second stop member 126 for restricting passage through the second eyelet 122, and a second tag 128. One or both of the second stop member 126 and the second tag 128 is coded to visually distinguish the second suture element 110 from the first suture element 124.

As illustrated, suture anchor 102 can include at least one fixation feature 130 for engaging bone and fixing the suture anchor 102 into bone 132. In one embodiment, the suture anchor 102 is fixed in the bone 132 such that it is positioned entirely below the surface 134 of the bone's cortical layer 136. The feature 130 can comprise any type of conventional fixation features suitable for fixing the anchor to bone, including one or more of screw threads, ridges, barbs, one or more toggle members, an expandable outer surface, or an adhesive.

Figure 2:
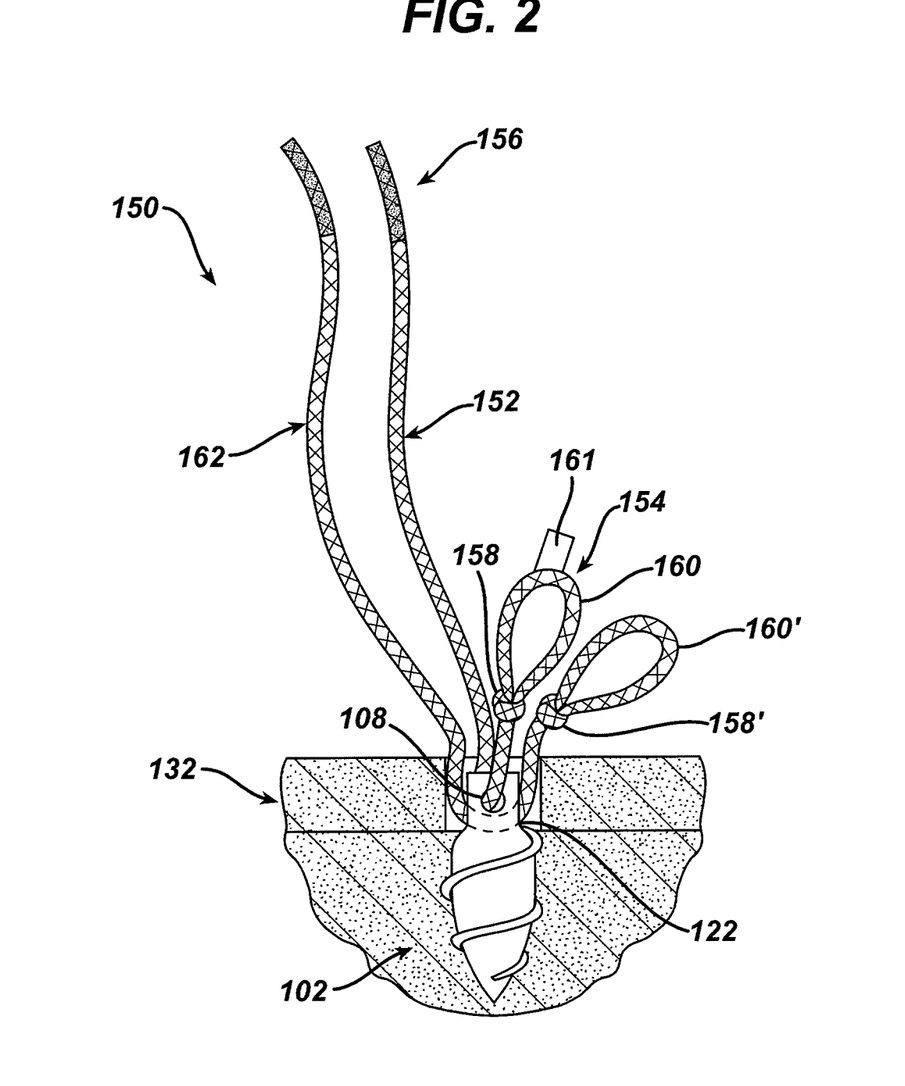
FIG. 2 illustrates an embodiment of a suture anchor assembly according to the present invention including sutures terminating in loops and mounted to a suture anchor.

FIG. 2 illustrates another embodiment in which a suture anchor assembly 150 is loop-terminated. The loop-terminated assembly 150 resembles the tag-terminated assembly 100, except that the loop-terminated assembly 150 includes closed loops of material in place of the tags 118, 128 of the tag-terminated assembly 100. A first loop-ended suture element 152 having a first end 154 and a second end 156 is shown to be mounted through the first eyelet 108. The first end 154 of the first loop-ended suture element 152 can include a first stop member 158 and a first loop 160. In one embodiment the first stop member 158 can be a knot that closes the first loop 160 and that is dimensioned so that it cannot readily pass through the first eyelet 108, thereby preventing the first loop-ended suture element 152 from being demounted from the anchor 102 by pulling the second end 156. The assembly 150 can further include a second loop-ended suture element 162 having a second loop 160' and a second stop member 158' mounted to the second eyelet 122. The second loop-ended suture element 162 resembles the first loop-ended suture element 152, but it can be visually coded so that the first 152 and second 162 suture elements can be uniquely identified with respect to one another. In another embodiment, three or more suture elements can be mounted to the anchor 102. The loops 160, 160' may be formed in the suture or they may be separate loops that are attached to the ends of the suture.

Although not necessary, at least one loop 160, 160' may optionally include an additional feature, such as a tag 161, formed thereon.

In one embodiment the stop member 158, 158' is a knot that can be in the form of a fixed knot. In another embodiment the stop member 158, 158' is a knot in the form of a slipknot such that the size of first and second loops 160, 160' is adjustable. In one embodiment, a loop associated with a suture element according to the present invention is incorporated into a suture knot formed as part of a surgical repair procedure. In a further embodiment, the loop incorporated into the suture knot is itself fastened using a slipknot and the loop is cinched closed along with tying suture for the repair procedure. In another embodiment one or more additional suture elements can be passed through the loop 160, 160', followed by one or more of cinching and tying the loop to permanently couple the one or more additional suture elements to the loop.

One skilled in the art will appreciate that first and second stop members 158, 158' can be of any construction compatible with positioning in a living body during a surgical procedure, and sized to prevent its passage through the first eyelet 108. In other embodiments, the first and second stop members 158, 158' is one or more of a crimp, a bead bonded to the first suture element, heat shrinkable tubing, a compression fitting, or another type of stop member. In an embodiment, the stop members 158, 158' are visually coded to be physically distinguishable each other or from a stop member on other suture elements. In this way it is possible to associate a given stop member, such as the first stop member 158, with another portion of the first suture element 152, for example, the second end 156. The stop elements 158, 158' can be integral with the loop 160, 160' attached to the same suture element, or the stop elements can be separate from such a loop.

Figure 3A:
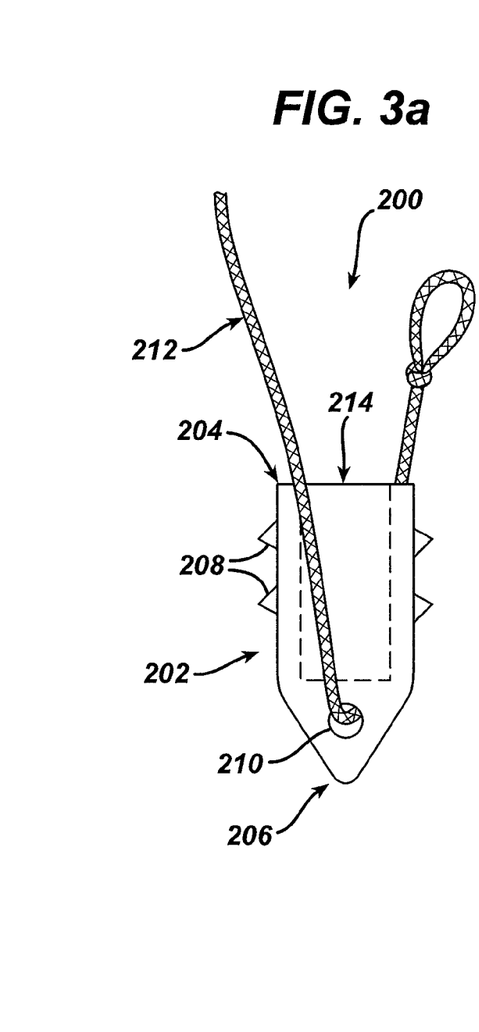
FIG. 3a illustrates an embodiment of a suture anchor assembly according to the present invention including a suture anchor having a distally positioned suture eyelet.

Suture anchors used in assemblies according to the present invention can include eyelets or other suture-mounting features at any location on or associated with the suture anchor. As illustrated in FIGS. 1 and 2, for example, a suture eyelet can be located near the proximal end 104 of the anchor 102 for use in an assembly according to the present invention. FIG. 3a illustrates an embodiment of a suture anchor assembly 200 wherein an anchor 202 having a proximal end 204, a distal end 206, and bone-fixation features 208 as described above, includes one or more suture eyelets 210 positioned near the distal end 206. The assembly 200 also comprises one or more suture elements 212 with a tag or a loop termination at one end as described above. In one embodiment, as shown, the suture anchor 202 can have a proximal opening 214 for internal engagement with an inserter for assisting in fixing the anchor 202 in bone. In other embodiments, eyelets for passing suture can be intermediately positioned between a proximal and distal end of an anchor. In yet another embodiment, an eyelet can be in the form of a flexible loop that extends from a surface of an anchor.

Figure 3B:
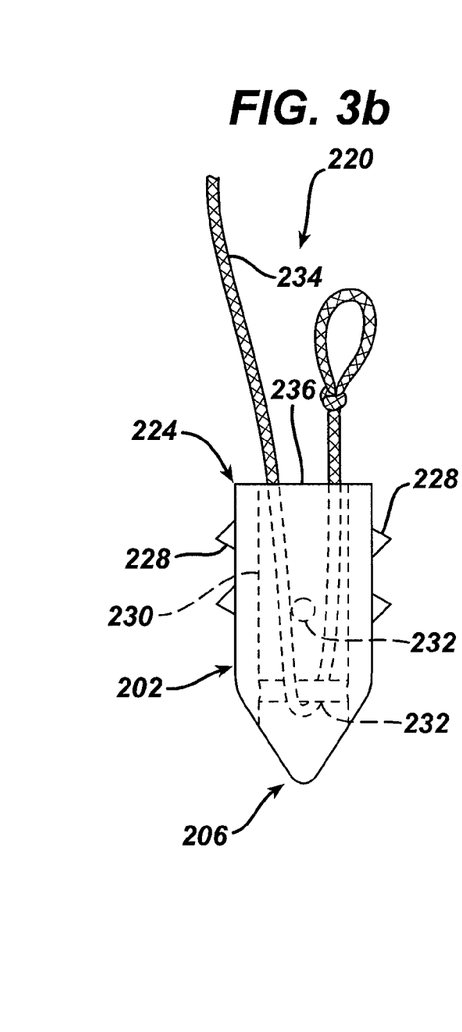
FIG. 3b illustrates an embodiment of a suture anchor assembly according to the present invention including a suture anchor having an internal suture-mounting member.

FIG. 3b illustrates another embodiment of a suture anchor assembly 220 according to the present invention, including a suture anchor 222 having a proximal end 224, a distal end 226, and external bone-fixation features 228 as described above. As shown, the anchor can also include a longitudinal passage 230 and at least one internal member 232, which can be transverse to the passage 230 about which one or more suture elements 234 of the type described above can be passed. Further, each suture element 234 can have a tag or a loop termination at one end as described above. Each internal member 232 can be integral to the body of the anchor 222, or it can be a cross-member positioned substantially transversely to the longitudinal passage 230. The proximal end 236 of the longitudinal passage 230 can be adapted for internal engagement with an inserter for assisting in fixing the anchor 222 in bone. In one embodiment, the suture assembly 220 includes two suture elements mounted to the anchor 222. In another embodiment, the suture assembly includes three or more suture elements mounted to the suture anchor 222.

Figure 3C:
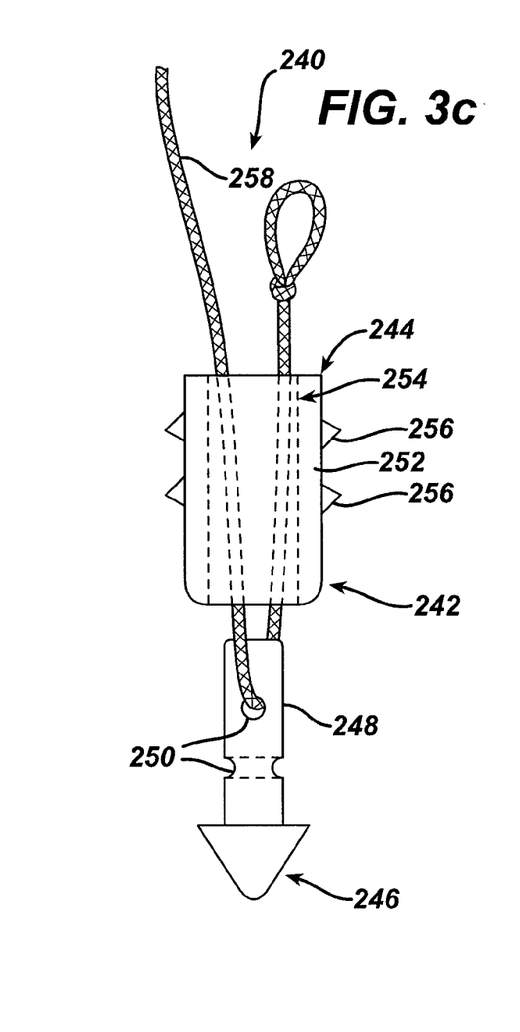
FIG. 3c illustrates an embodiment of a suture anchor assembly according to the present invention including a multi-part suture anchor having a suture-mounting member.

FIG. 3c illustrates yet another embodiment of a suture anchor assembly 240 according to the present invention, The assembly 240 is seen to include a suture anchor 242 having a proximal end 244, a distal end 246, an inner body portion 248 having at least one suture-mounting passage 250, and an outer body portion 252 having a channel 254 for receiving the inner portion 248 and bearing one or more bone fixation features 256. The inner portion 248 can be configured to slidably fit into the channel 254 to assemble the anchor 242. The assembly 240 can also include at least one suture element 258 of the type having a tag or a loop termination of the type described above. In one embodiment, the suture element 258 is mounted through a corresponding passage 250 before the inner body portion 248 is assembled to the outer body portion 254. In a further embodiment, the outer body portion 254 can be expandable to assist in fixing the anchor 242 into bone. In yet another embodiment, assembly of the inner body portion 248 fully into the outer body portion 254 can lock the position of the suture element 252 with respect to the anchor 242. In one embodiment, the suture assembly 240 includes two suture elements 252 mounted to the anchor 242. In another embodiment, the suture assembly includes three or more suture elements 252 mounted to the suture anchor 242.

Figure 4:
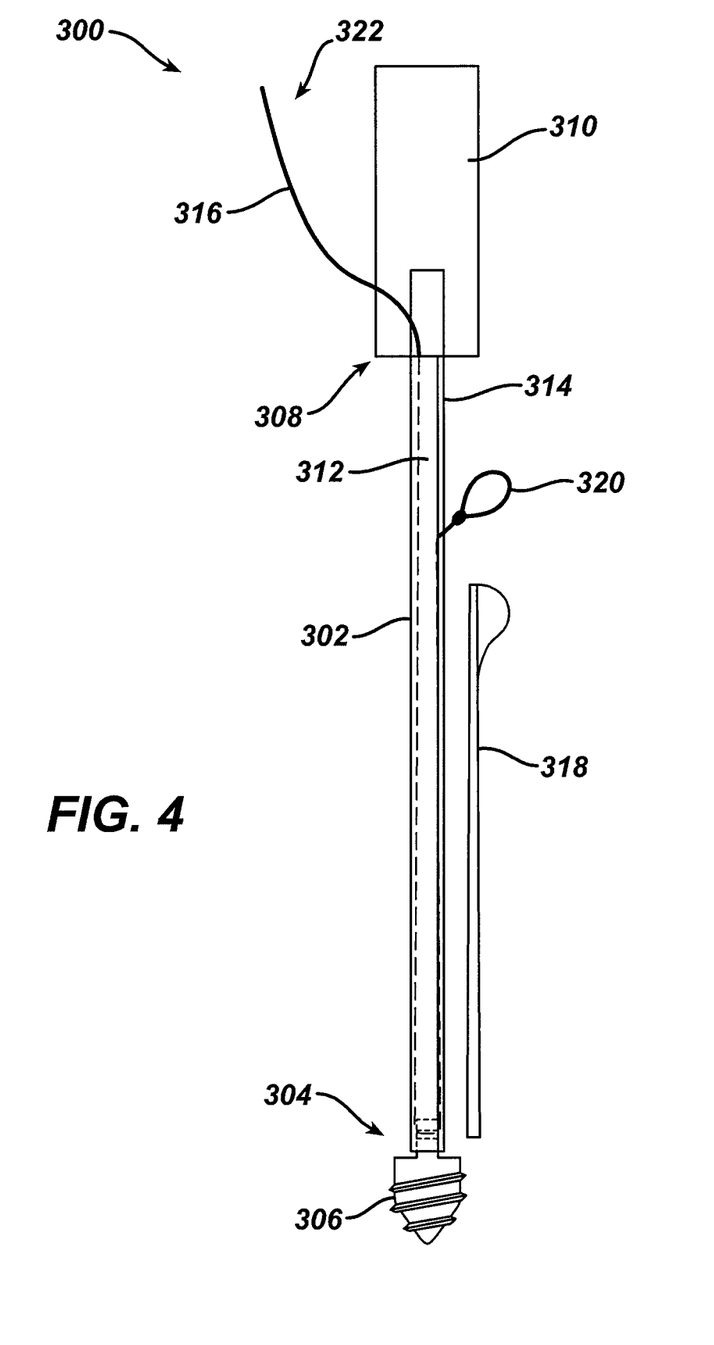
FIG. 4 illustrates an embodiment of an anchor inserter according to the present invention.

One embodiment of an insertion tool 300 useful in accordance with the present invention is illustrated in FIG. 4. As illustrated, the insertion tool 300 can include a shaft 302 having a distal end 304 adapted for mounting to a suture anchor 306, and a proximal end 308 connected to a handle 310. In various embodiments, the shaft 302 is adapted to engage an external portion of the anchor 306 (as illustrated in FIG. 4). Although not illustrated, one skilled in the art will appreciate that the shaft 302 can alternatively engage an internal portion of an anchor, for example, to engage the anchor types illustrated in FIG. 3a or 3b.

In one embodiment, the shaft 302 is at least one of partially cannulated, having a lumen 312 extending at least partially therethrough. Further, one or more slots 314 can extend from lower 312 through shaft 302 for receiving a portion of one or more suture elements 316 of the type described above and mounted to the suture anchor 306. In one embodiment, a slot cover 318 can be used to retain each suture element in the slot 314 during insertion of the anchor 306 into bone.

In one embodiment, the inserter 300 is adapted for pushing an anchor 306 into a bone hole. In another embodiment, the inserter 300 is adapted at the distal end 304 to rotationally engage the suture anchor 306 to drive the anchor 306 into bone.

In another embodiment, the suture element 316 can include a suture loop 320 that is positioned proximally along the shaft 302 for insertion and fixation of the suture anchor 306 into bone, following which a free end 322 of the suture element 316 is pulled to position the suture loop 320 distally, in proximity to the suture anchor 306, until used by the surgeon to connect the suture element 316 to tissue.

Figure 5A:
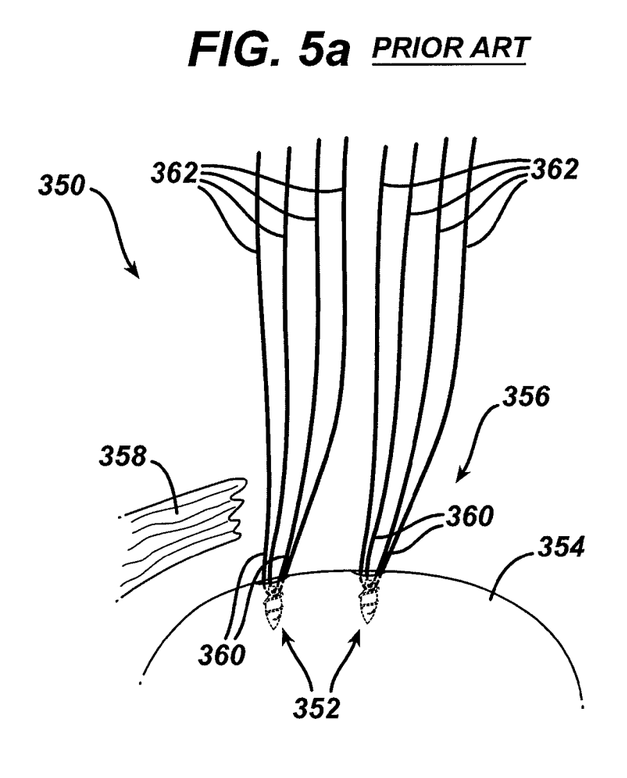
FIG. 5a illustrates a prior art arrangement of sutures about a surgical site.

Surgical repair procedures using suture assemblies according to the present invention can dramatically reduce the number of suture legs that emerge from a surgical site and that require management during a surgical procedure, relative to known suture anchor assemblies and methods. FIG. 5a illustrates a prior art example 350 of two suture anchors 352 fixed in a bone 354 at a surgical site 356, in preparation for repairing soft tissue 358 by attaching it to the bone 354. Each of the two anchors 352 include two sutures 360 mounted thereon, resulting in eight suture legs 362 emerging from the surgical site and requiring management by the surgeon.

Figure 5B:
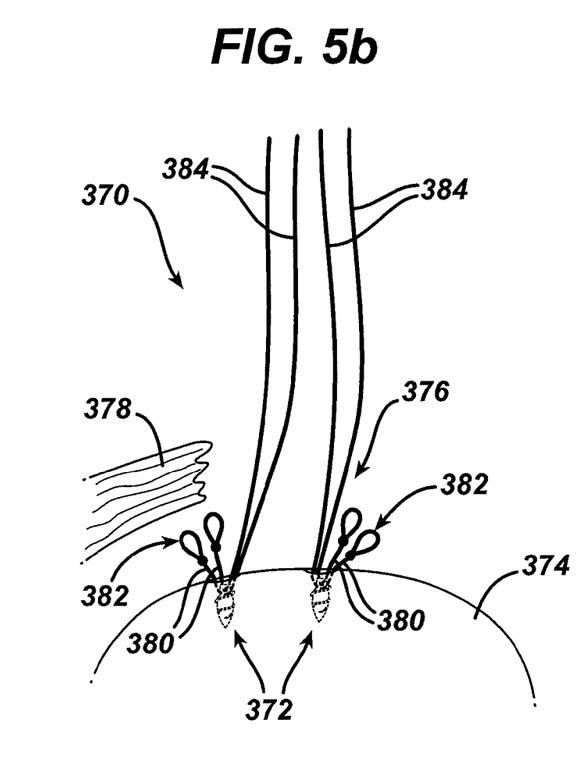
FIG. 5b illustrates an embodiment of suture management about a surgical site using suture anchor assemblies according to an embodiment of the present invention.

FIG. 5b illustrates an example 370 of suture management for a repair similar to that described in association with FIG. 5a, but using suture assemblies according the present invention. In FIG. 5b, two suture anchors 372 are fixed in a bone 374 at a surgical site 376 in preparation for repairing soft tissue 378 to the bone 374. Two loop-ended suture elements 380 as described above are mounted to each of the two anchors 372, with respective suture loops 382 positioned in proximity to the respective anchors 372. As illustrated only four suture legs 384 lead from the surgical site 376, halving the number of suture legs requiring active management, relative to the illustration of FIG. 5a. Thus eight limbs of suture are managed with only four limbs exiting the surgical site. When ready to use a specific suture element for a repair step, the surgeon can grasp or hook the associated loop to pull a portion of the suture element slidably through an eyelet of the anchor, for passing through or around tissue, for tying, or cutting as needed.

In another embodiment, a suture anchor assembly according to the present invention is provided as a kit including a suture anchor mounted to an insertion tool, and one or more visually coded suture element as described above, premounted to the anchor. In a further embodiment, several different kits are provided, each having unique visual coding of included suture elements, thereby enabling the surgeon to take additional advantage of the suture management capabilities of the present invention for multi-anchor procedures. In an exemplary surgical procedure according to the present invention, the surgeon inserts an anchor into bone at a surgical site, using, for example, an anchor that is premounted onto an inserter device and preloaded with one or more suture elements including loops or tags. The surgeon then removes the inserter, leaving the anchor and one or more suture element in place at the surgical site. The surgeon then moves the external (non-loop) limbs of suture to an access portal and passes one or both of the external and loop-bearing limbs through tissue. When ready to tie a knot, the surgeon grasps the visually coded loop as required and pulls it out of the working portal. Then the surgeon ties the knot and removes the loop as or if required.

The sutures used in the assemblies of the present invention can be made from conventional biocompatible materials, both absorbable and non-absorbable. Exemplary materials include but are not limited to polyester, polyethylene, polypropylene, silk, polydioxanone, PLA, PGA, copolymers and the like and equivalents thereof.

Suture anchor assemblies and their application according to the present invention have many advantages. These advantages include, but are not limited to, advantages associated with ease of use for the surgeon and probable reductions in surgical time and skill required to perform soft tissue repairs to bone. Using suture anchor assemblies according to the present invention also reduces the number of suture limbs requiring management about a surgical site, thereby reducing possible confusion and risk of tangling associated with having many suture limbs routed through arthroscopic surgical portals. A loop or flag end of a suture element can be kept near its associated suture anchor until needed by the surgeon, at which time it can be grasped by the surgeon and pulled through a surgical portal to tie knots or to otherwise effect the repair. Suture anchor assemblies of the present invention can also include visual coding such as color coding of suture ends, flags, stops and loops, to help distinguish one suture element from another, thereby further improving the ease of suture management with the present invention.

Another advantage is that stop members on suture elements according to the present invention assist in preventing suture elements from being accidentally demounted from a suture anchor installed in a bone. In addition, suture loops associated with suture elements of the present invention assist identification and handling of suture elements during a surgical procedure.

Although this invention has been shown and described with respect to detailed embodiments thereof, it will be understood by those skilled in the art that various changes in form and detail thereof may be made without departing from the spirit and scope of the claimed invention.

What is claimed is:

1. A surgical repair assembly comprising:
   at least one suture anchor having a suture anchor body with at least one eyelet configured to enable a suture to be passed therethrough, and at least one fixation feature on the anchor body for engaging bone; and
   a first suture element passing through a respective one of the at least one eyelets, the first suture element having a first end, a second end and a suture diameter configured to enable it to pass slidably through the respective eyelet, the first end terminating in a unique identifying feature and having an adjacent stop member sized to be too large to pass through the respective eyelet;

a second suture element passing through a respective one of the at least one eyelets, the second suture element having a first end, a second end and a suture diameter configured to enable it to pass slidably through the respective eyelet, the first end terminating in a unique identifying feature comprising a size or shape different than a size or shape of the unique identifying feature of the first suture element and having an adjacent stop member sized to be too large to pass through the respective eyelet.

2. The assembly of claim 1, wherein the unique identifying feature is at least one of a tag and a suture loop.

3. The assembly of claim 1, wherein the identifying feature on the first suture element is a visual indicator having a distinguishing characteristic selected from the group consisting of a pattern, a shape, a tactile feature, and combinations thereof.

4. The assembly of claim 3, wherein a distinguishing characteristic is formed on the second end of the first suture element correlating to the unique identifying feature at the first end of the first suture element.

5. The assembly of claim 1, wherein the stop on the first suture element is selected from the group consisting of a knot, a crimp, a bead, heat shrinkable tubing, and a compression fitting.

6. The assembly of claim 1, wherein the stop on the first suture element comprises the unique identifying feature.

7. The assembly of claim 1, wherein the unique identifying feature of the first suture element is a suture loop and wherein the stop on the first suture element is a knot.

8. The assembly of claim 7, wherein the knot is a slip knot.

9. The assembly of claim 7, wherein the knot is spaced from the suture loop.

* * * * *